United States Patent [19]

Rigterink

[11] 4,170,657

[45] Oct. 9, 1979

[54] SUBSTITUTED(((PHENYL)AMINO)CARBONYL)-BENZAMIDES

[75] Inventor: Raymond H. Rigterink, Midland, Mich.

[73] Assignee: The Dow Chemical Company, Midland, Mich.

[21] Appl. No.: 796,645

[22] Filed: May 13, 1977

[51] Int. Cl.$^2$ .................. A01N 9/12; A01N 9/20; C07C 127/17; C07C 127/22
[52] U.S. Cl. .................. 424/322; 260/553 E; 260/553 A
[58] Field of Search .................. 260/553 E, 553 A; 424/322

[56] References Cited

U.S. PATENT DOCUMENTS

| | | | |
|---|---|---|---|
| 3,748,356 | 7/1973 | Wellinga et al. | 260/553 E |
| 3,933,908 | 1/1976 | Wellinga et al. | 260/553 E |
| 3,935,258 | 1/1976 | Hempel et al. | 260/553 A |
| 3,984,468 | 10/1976 | Klauke et al. | 260/553 A |
| 4,013,717 | 3/1977 | Wellinga et al. | 260/553 E |
| 4,041,177 | 8/1977 | Sirrenberg et al. | 260/553 E |
| 4,068,002 | 1/1978 | Sirrenberg et al. | 260/553 E |
| 4,085,226 | 4/1978 | Sirrenberg et al. | 260/553 E |
| 4,089,975 | 5/1978 | Wade et al. | 260/553 E |

FOREIGN PATENT DOCUMENTS 2024249 12/1971 Fed. Rep. of Germany ...... 260/553 A
1501607 2/1978 United Kingdom.

*Primary Examiner*—Thomas Waltz
*Assistant Examiner*—Raymond Covington

[57] ABSTRACT

Novel alkoxy or alkylthio substituted(((phenyl)amino)-carbonyl)-benzamides are disclosed. The compounds of the instant invention are useful as insecticides and can be formulated to provide insecticidal compositions.

31 Claims, No Drawings

SUBSTITUTED(((PHENYL)AMINO)CARBONYL)-BENZAMIDES

BACKGROUND OF THE INVENTION

Halogen substituted((phenylamino)carbonyl)-benzamides are known in the art as, for example, in U.S. Pat. No. 3,748,356; U.S. Pat. No. 3,450,747, and Belgian Pat. No. 833,288.

DESCRIPTION OF THE INVENTION

The novel compounds of this invention are of the formula

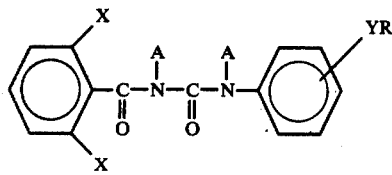

wherein
  each X substituent is individually chosen from the group consisting of H, Cl, F, Br, $CR_3'$ and $OCR_3'$, wherein each $R'$ substituent is individually, either $R''$ or H, with $R''$ being selected from the group consisting of F, Cl and Br, with the proviso that both X substituents are not H;
  each A substituent is individually chosen from the group consisting of $CH_3$ and H, with the proviso that both A substituents are not $CH_3$;
  Y represents S or O; and
  R represents a halogenated alkyl group having up to 3 carbon atoms.

The term "active ingredients" is at times used hereinafter in this specification to broadly describe the compounds of the present invention.

The active ingredients of the present invention are normally crystalline solids which are of low solubility in water and of moderate solubility in many organic solvents. These active ingredients have low phytotoxicity to plants and have exceptional activity in the kill and control of such insects as the cabbage looper, beet army worm, and the larvae of mosquitoes, hornflies and houseflies. These active ingredients may be formulated with the usual insecticide carriers, well known to those skilled in the art, to provide insecticidal compositions.

The compounds of the present invention may be prepared via several methods hereinafter set forth. One common method is to react an appropriate benzoyl isocyanate derivative with an appropriate anisidine or phenetidine derivative in the presence of an organic solvent. The following reaction scheme illustrates this method of preparing the compounds of the present invention:

Method A

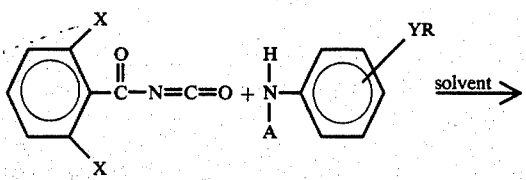

-continued

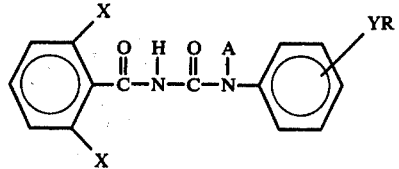

wherein
  X, A, Y and R are as set forth above.

The reaction is carried out by contacting the reactants together in equimolar proportions in the presence of a solvent at a reaction temperature which, at atmospheric pressure, may vary from 0° C. to the boiling point of the solvent used. Examples of suitable solvents are aromatic hydrocarbons such as benzene or xylene, chlorinated hydrocarbons such as chloroform, methylene chloride or ethylene chloride or other inert solvents such as acetonitrile.

Following the completion of the reaction (generally lasting from about 0.5 to about 24 hours), the mixture is cooled and the precipitated product is collected by filtration or other suitable techniques. This product usually is washed with a solvent such as hexane and dried. The resulting crude product may be further purified, if desired, by recrystallization from a solvent such as aqueous acetic acid or by other purification procedures.

Compounds of the present invention may also be produced by:

Method B

Reacting a compound of the formula

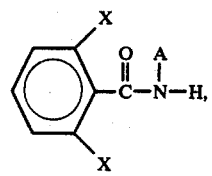

where X and A have the aforementioned meanings, with a compound of the formula

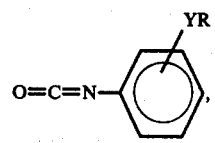

where R and Y have the aforementioned meanings, preferably in equimolar proportions in a reaction mixture containing pyridine and sodium in a suitable solvent so as to obtain the corresponding compound of the present invention.

Method C

Reacting a compound of the formula

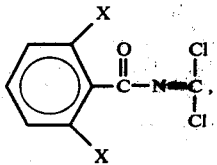

where X has the aforementioned meaning, with a compound of the formula

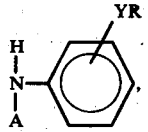

where A, Y, and R have the aforementioned meanings, in the presence of a solvent such as benzene or toluene and a base (such as triethylamine or 3,4-dichloroaniline) capable of binding the hydrogen chloride evolved so as to obtain an intermediate compound of the formula

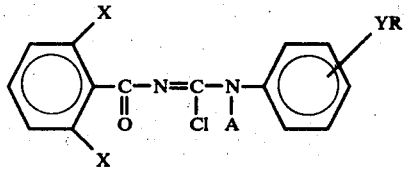

which is hydrolyzed such as by agitation in water so as to obtain the corresponding compound of the present invention.

Method D

Reacting a compound of the formula

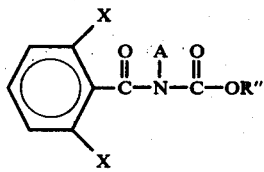

where R" is an alkyl group having from about 1 to about 4 carbon atoms and A and X have the aforementioned meanings, with a compound of the formula

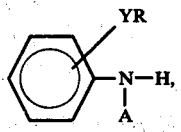

where R, Y and A have the aforementioned meanings, in the presence of an inert solvent such as xylene or chlorobenzene so as to obtain the corresponding compound of the present invention.

Method E

Reacting a compound of the formula

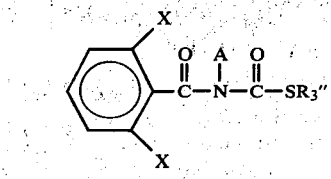

where X, R" and A have the aforementioned meanings, with a compound of the formula

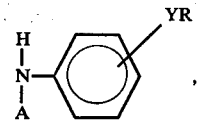

where A, Y and R have the aforementioned meanings, in equimolar proportions in the presence of a solvent such as toluene so as to obtain the corresponding compound of the present invention.

DESCRIPTION OF SOME PREFERRED EMBODIMENTS

The following examples illustrate the present invention and the manner by which it can be practiced but as such should not be construed as limitations upon the overall scope of the same. The product compounds are identified by elemental analysis and/or nuclear magnetic resonance spectroscopy.

EXAMPLE 1—Preparation of 2,6-Dichloro-N-(((4-trifluoromethoxy)phenyl)amino)-carbonyl)-benzamide Five grams (0.03 mole) of α,α,α-trifluoro-p-anisidine and 6.5 grams (0.03 mole) of 2,6-dichlorobenzoyl isocyanate were added to 100 milliliters of benzene and heated under reflux with stirring for 1 hour. The benzene was removed by evaporation. The solid residue was slurried in 100 milliliters of cold hexane. The residual material was collected by filtration, washed with hexane and dried, leaving a crude product which was a white solid melting at 170°–180° C. This was purified by recrystallization from 60 milliliters of 85 percent of aqueous acetic acid. The yield was 7 grams (61 percent of theoretical) of a white solid melting at 188°–190° C.

The structure of the product was confirmed by nuclear magnetic resonance spectroscopy (NMR) as being

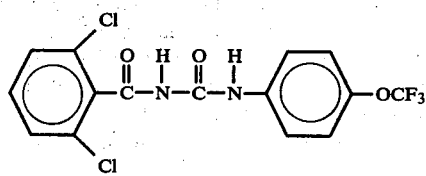

Elemental Analysis—Theory: C, 45.82%; H, 2.31%; N, 7.13%. Found: C, 45.60%; H, 2.41%; N, 7.24%.

EXAMPLE 2—Preparation of 2,6-Dichloro-N-(((4-(2,2-dichloro-1,1-difluoroethoxy)-phenyl)amino)carbonyl)-benzamide In 200 milliliters of xylene, 11.5 grams (0.04 mole) of β,β-dichloro-α,α-difluoro-p-phenetidine.HCl and 3.6 grams (0.04 mole) of 2,6-dichlorobenzoyl isocyanate were refluxed with stirring for two hours. The xylene was thereafter removed by vacuum distillation. The residue which remained was mixed with 200 milliliters of hexane and a crystalline solid precipitated. This precipitated material was collected by suction filtration, washed with hexane and dried. The dried crude product was a light tan gummy solid melting at 160°–185° C. This crude product was purified by recrystallization from 60 milliliters of 83 percent aqueous acetic acid, leaving 85 grams of a white solid melting at 211°–213° C. (56 percent of theoretical). Nuclear magnetic resonance spectroscopy confirmed the structure as being Elemental Analysis—Theory: C, 41.95%; H, 2.20%; N, 6.12%. Found: C, 41.8%; H, 2.17%; N, 6.33%.

Using methods in accordance with those detailed above, the compounds of Examples 3–27 were prepared. These compounds and their melting points are set forth in Table 1.

TABLE 1

| Example | Compound | Melting pt. (°C.) |
| --- | --- | --- |
| 3 | 2-Chloro-N-(((4-(trifluoromethoxy)phenyl)amino)carbonyl)-benzamide | 188—190 |
| 4 | 2-Trifluoromethyl-N-(4-trifluoromethoxy)phenyl)amino)carbonyl)-benzamide | 157—159 |
| 5 | 2,6-Dichloro-N-(((4-(1,1,2,2-tetrafluoroethoxy)phenyl)amino)carbonyl)-benzamide | 187—189 |
| 6 | 2,6-Difluoro-N-(((4-(1,1,2,2-tetrafluoroethoxy)phenyl)amino)carbonyl)-benzamide | 212—215 |
| 7 | 2,6-Difluoro-N-(((4-(2,2-dichloro-1,1-difluoroethoxy)phenyl)-amino)carbonyl)-benzamide | 216—218 |
| 8 | 2,6-Difluoro-N-(((4-(trifluoromethoxy)phenyl)amino)carbonyl)-benzamide | 220—222 |
| 9 | 2,6-Difluoro-N-(((2-(2,2-dichloro-1,1-difluoroethoxy)phenyl)-amino)carbonyl)-benzamide | 161—164 |
| 10 | 2,6-Difluoro-N-(((4-((2,2-dichloro-1,1-difluoroethyl)thio)phenyl)-amino)carbonyl)-benzamide | 197—199 |
| 11 | 2,6-Dimethoxy-N-(((4-(1,1,2,2-tetrafluoroethoxy)phenyl)amino)carbonyl)-benzamide | 151—154 |
| 12 | 2,6-Dichloro-N-(((2-(2,2-dichloro-1,1-difluoroethoxy)phenyl)-amino)carbonyl)-benzamide | 206—208 |
| 13 | 2,6-Dichloro-N-(((4-((2,2-dichloro-1,1-difluoroethyl)thio)phenyl)-amino)carbonyl)-benzamide | 208—211 |
| 14 | 2-Chloro-N-(((2-(2,2-dichloro-1,1-difluoroethoxy)phenyl)amino)car- | 152—154 |
| 15 | 2-Chloro-N-(((4-(2,2-dichloro-1,1-difluoroethoxy)phenyl)amino)-carbonyl)-benzamide | 142—145 |
| 16 | 2-Chloro-N-(((4-(1,1,2,2-tetrafluoroethoxy)phenyl)amino)carbonyl)-benzamide | 192—194 |
| 17 | 2-Chloro-N-(4-(((2,2-dichloro-1,1-difluoroethylthio)phenyl)amino)-carbonyl)-benzamide | 150—153 |
| 18 | 2,6-Dichloro-N-(((4-(2,2-dichloro-1,1-difluoroethoxy)phenyl)-amino)carbonyl)-N-methylbenzamide | 120—124 |
| 19 | 2,6-Dichloro-N-(((4-(2,2-dichloro-1,1-difluoroethoxy)phenyl)-methylamino)carbonyl)-benzamide | 159—163 |
| 20 | 2,6-Difluoro-N-(((4-(2,2-dichloro-1,1-difluoroethoxy)phenyl)-methylamino)carbonyl)-benzamide | 98—100 |
| 21 | 2,6-Dibromo-N-(((4-(1,1,2,2-tetrafluoroethoxy)phenyl)amino)car-bonyl)-benzamide | 197—199 |
| 22 | 2-Bromo-N-(((4-(1,1,2,2-tetrafluoroethoxy)phenyl)amino)carbonyl)-benzamide | 184—186 |
| 23 | 2-Chloro-N-(((4-(2,2-dichloro-1,1-difluoroethoxy)phenyl)methyl-amino)carbonyl)-benzamide | 99—103 |
| 24 | 2-Fluoro-N-(((4-(1,1,2,2-tetrafluoroethoxy)phenyl)amino)carbonyl)-benzamide | 182—184 |
| 25 | 2-Trifluoromethyl-N-(((4-(2,2-dichloro-1,1-difluoroethoxy)phenyl)-methylamino)carbonyl)-benzamide | 100—102 |
| 26 | 2,6-Difluoro-N-(((3-(2,2-dichloro-1,1-difluoroethoxy)phenyl)-amino)carbonyl)-benzamide | 177—179 |
| 27 | 2,6-Dichloro-N-(((3-(2,2-dichloro-1,1-difluoroethoxy)phenyl)-amino)carbonyl)-benzamide | 188—192 |
| 28 | 2,6-Difluoro-N-(((4-((1,1,2,2-tetrafluoroethyl)thio)phenyl)-amino)carbonyl)-benzamide | 198—200 |
| 29 | 2,6-Dichloro-N-(((4-((1,1,2,2-tetrafluoroethyl)thio)phenyl)-amino)carbonyl)-benzamide | 219—221.5 |

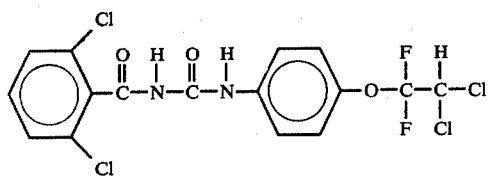

The isocyanate starting material for Method A is synthesized by treating the corresponding benzamide with oxalyl chloride in the presence of a solvent such as a chlorinated hydrocarbon.

The anisidine starting material of Method A is known in the prior art and may be made by the procedure delineated in C.A.51:15518C. Phenetidine starting materials can be prepared by the procedure set forth in C.A.76:P722169 (Ger. Offen. No. 2,029,556).

Examples of other methods of making the starting material for Method A are shown in U.S. Pat. No. 3,748,356.

The compounds of the present invention have been found to be useful in methods for the killing and control of various undesirable agricultural and household insects such as cabbage looper, beet army worm and the larvae of mosquitoes, hornflies and houseflies. The compounds are highly active and can be employed to both kill insects outright and/or to prevent adult emergence from juvenile forms of the insect. In such applications, the insect to be controlled and/or its habitat is contacted or treated with an insecticidal amount of one or more of the compounds of the present invention.

For all such uses, these compounds can be employed in unmodified form. However, the present invention embraces the use of an insecticidally-effective amount of the active ingredients in composition form with a material known in the art as an adjuvant or carrier.

Thus, for example, compositions employing one or a combination of these active ingredients can be in the form of a liquid or a dust; and the adjuvant employed can be any one of a plurality of materials including aromatic solvents, petroleum distillates, water or other liquid carriers, propellant substances, surface-active dispersing agents, light absorbers and finely-divided carrier solids.

The exact concentration of one or a combination of the compounds of the present invention in a composition thereof with an adjuvant therefor can vary; it is only necessary that one or a combination of the compounds be present in a sufficient amount so as to make possible the application of an insecticidally-effective or inactivating dosage.

Suitable adjuvants of the foregoing type are well known to those skilled in the art. The methods of applying the solid or liquid insecticidal formulations are similarly well known in the art.

The insecticidally-effective dosage desirable for effective use of preparations containing active compounds will naturally depend on various factors such as the active ingredient or ingredients chosen and the form of preparation. Moreover, the activities of the compounds of the present invention against different insects will vary from compound to compound. Generally, for practical applications, one or a combination of these active ingredients can be broadly applied to the insect larvae or their habitat in compositions containing from about 0.0001 percent to about 98 percent by weight of the compounds.

In the preparation of dust compositions, these compounds can be compounded with any of the finely-divided carrier solids such as pyrophyllite, diatomaceous earth, gypsum and the like. In such operations, the finely-divided carrier is ground or mixed with one or a combination of the compounds, as active agent(s), or wetted with a solution of the active agent(s) in a volatile organic solvent. Similarly, dust compositions can be compounded with various solid dispersing agents, such as fuller's earth, attapulgite and other clays. These dust compositions can be employed as treating compositions or can be employed as concentrates and subsequently diluted with additional solid dispersing agents or with pyrophyllite, diatomaceous earth, gypsum and the like to obtain the desired amount of active agent in a treating composition. Also, such dust compositions can be dispersed in water, with or without the aid of a surfactant, to form spray mixtures.

Furthermore, one or a combination of the compounds or a dust concentrate composition containing such compound(s) can be incorporated in intimate admixture with surface-active dispersing agents such as ionic and nonionic emulsifying agents to form spray concentrates. Such concentrates are readily dispersible in liquid carriers to form sprays containing the toxicant(s) in any desired amount. The choice of the dispersing agent and amount thereof employed are determined by the ability of the agent to facilitate the dispersion of the concentrate in the liquid carrier to produce the desired spray composition.

In the preparation of liquid compositions, one or a combination of the products can be compounded with a suitable water-immiscible organic liquid and surface-active dispersing agent to produce an emulsifiable liquid concentrate which can be further diluted with water and oil to form spray mixtures in the form of oil-in-water emulsions. In such compositions, the carrier comprises an aqueous emulsion, that is, a mixture of water-immiscible solvent, emulsifying agent and water. Preferred dispersing agents to be employed in these compositions are oil soluble and include the nonionic emulsifiers such as the polyoxyethylene derivatives of sorbitan esters, complex ether alcohols and the like. However, soil-soluble-ionic emulsifying agents such as mahogany soaps can also be used. Suitable organic liquids to be employed in the compositions include petroleum oils and distillates, toluene, liquid halohydrocarbons and synthetic organic oils.

An aerosol preparation according to the invention is obtained in the usual manner by incorporating the active substance and a solvent in a volatile liquid suitable for use as a propellant, such as the mixture of chlorine and fluorine derivatives of methane and ethane commercially available under the trademark FREON ®.

Fumigating candles or fumigating powders, i.e., preparations which when burning are capable of emitting a pesticidal smoke, are obtained by taking up the active substance in a combustible mixture which may contain: (a) a sugar or a wood, preferably in ground form, as a fuel; (b) a substance to maintain combustion such as, for example, ammonium nitrate or potassium chlorate and (c) a substance to retard the combustion such as, for example, kaolin, bentonite and/or colloidal silicic acid.

When utilizing the active ingredients of the present invention as insecticides, one or a combination of the active ingredients or a composition containing such is applied to the insects or insect larvae directly, or by means of application to their habitat in any convenient manner, for example, by means of hand dusters or sprayers or by simple mixing with the food to be ingested by the insects or larvae. Application to the foliage of plants is conveniently carried out with power dusters, broom sprayers and fog sprayers. In such foliar applications, the compositions to be employed should not contain any appreciable amounts of any phytotoxic diluents. In large scale operations, dusts or low volume sprays can be applied from an airplane.

In representative activity tests, compounds of the present invention were formulated into emulsifiable solutions and added to cups containing water to thereby produce various concentrations of the compounds as the active toxicant in the water. Twenty third-stage larvae of the southern house mosquito, *Culex quinquefasciatus* Say, were added to the water in each cup and incubated at 80° F. until all adults had sufficient time to hatch. An untreated control was also incubated. After one week, all larvae in the control cup had hatched into normal adult mosquitoes. Table 2 sets forth the lowest concentration of each active compound which achieved 100% kill and control of the larvae directly or of the pupae as they began their moult into adults.

The compounds are referred to by their Example number.

TABLE 2

| Compound of Example Number | 2 | 4 | 5 | 7 | 8 | 10 | 11 | 13 | 15 | 17 | 26 |
|---|---|---|---|---|---|---|---|---|---|---|---|
| Lowest Concentration Achieving 100% Kill and Control (ppm) | 0.005 | 1 | 0.1 | 0.1 | 0.00025 | 0.0025 | 1.0 | 0.01 | 0.1 | 0.1 | 0.1 |

In additional representative activity tests, selected compounds of the present invention were formulated into emulsifiable solutions which were added to cups containing 200 grams of fresh cow manure. The compounds were added to the manure in 5 cubic centimeters of water and stirred thoroughly with a handheld electric mixer. The samples were seeded with 200 housefly eggs and allowed to incubate until all flies had completed their development and had emerged as adults. Percent control was determined by comparison with untreated samples and active compounds were retested at lower doses until a break point was found. Table 3 sets forth the lowest concentration of each active compound which achieved 100% kill and control of the larvae directly or of the pupae as they began their moult into adults.

TABLE 3

| Compound of Example Number | 5 | 6 | 10 | 13 | 16 | 17 |
|---|---|---|---|---|---|---|
| Concentration (ppm) | 50 | 10 | 50 | 50 | 10 | 25 |

The compounds set forth below were separately made into a water emulsion and mixed into 200 grams fresh cow manure. Approximately 500 hornfly eggs collected from colony flies were placed in the manure. The samples were allowed to incubate until all flies had completed their development and were emerging as adults. Percent control was determined by comparison with untreated samples and active compounds were related until a break point was found. Table 4 sets forth the lowest concentration of each active compound which achieved 100% kill and control of the larvae directly or of the pupae as they began their moult into adults.

TABLE 4

| Compound of Example Number | 5 | 6 | 7 | 10 | 11 | 13 | 15 | 16 | 17 | 22 | 24 | 28 | 29 |
|---|---|---|---|---|---|---|---|---|---|---|---|---|---|
| Concentration (ppm) | 50 | <0.1 | 1.0 | 0.5 | 10 | 10 | 25 | 10 | 1.0 | 10 | 25 | <25 | <1.0 |

In an additional operation, a representative compound of the present invention was tested for insecticidal performance against the cabbage looper in standard greenhouse and field testing procedures. The results of the operation are set forth in Table 5.

TABLE 5

| Compound of Example Number | Active Ingredient (Kilogram/Hectare) | Percent Larvae Mortality Cabbage Looper | |
|---|---|---|---|
| | | GHT | FT |
| 1 | 0.2 | 83 | 98 |
| 1 | 0.05 | 55 | 82 |

GHT = Greenhouse Test
FT = Field Test

In additional representative activity tests, compositions containing selected active ingredients of the present invention were applied to the habitat of beet army worm larvae (*Spodoptera exigera*). Table 6 sets forth the lowest concentration of each active ingredient, referred to by example number, which achieved 90% kill and control ($LC_{90}$) of the larvae.

TABLE 6

| Compound of Example Number | 1 | 2 | 5 | 6 | 7 | 8 | 13 | 15 | 17 | 18 | 19 | 28 | 29 |
|---|---|---|---|---|---|---|---|---|---|---|---|---|---|
| Lowest Concentration Achieving 90% Kill and Control | 5 | 8 | 7 | 67 | 102 | 10 | 19 | 100 | 62 | 11 | 75 | 46 | 13 |

What is claimed is:

1. A compound selected from the group consisting of 2-chloro-N-(((4-(trifluoromethoxy)phenyl)amino)carbonyl)-benzamide, 2-trifluoromethyl-N-(((4-(trifluoromethoxy)phenyl)amino)carbonyl)-benzamide, 2,6-difluoro-N-(((4-(1,1,2,2-tetrafluoroethoxy)phenyl)amino)carbonyl)-benzamide, 2,6-difluoro-N-(((4-(2,2-dichloro-1,1-difluoroethoxy)phenyl)amino)carbonyl)-benzamide, 2,6-difluoro-N-(((4-(trifluoromethoxy)phenyl)amino)carbonyl)-benzamide, 2,6-dichloro-N-(((4-(trifluoromethoxy)phenyl)amino)carbonyl)-benzamide, 2,6-dimethoxy-N-(((4-(1,1,2,2-tetrafluoroethoxy)phenyl)amino)carbonyl)-benzamide, 2,6-dichloro-N-(((2-(2,2-dichloro-1,1-difluoroethoxy)phenyl)amino)carbonyl)-benzamide, 2,6-dichloro-N-(((4-(2,2-dichloro-1,1-difluoroethoxy)phenyl)amino)carbonyl)-N-methylbenzamide, 2-chloro-N-(4-(((2,2-dichloro-1,1-difluoroethylthio)phenyl)amino)carbonyl)-benzamide, 2,6-dichloro-N-(((4-((2,2-dichloro-1,1-difluoroethyl)thio)phenyl)amino)carbonyl)-benzamide, 2-chloro-N-(((2-(2,2-dichloro-1,1-difluoroethoxy)phenyl)amino)carbonyl)-benzamide, 2-chloro-N-(((4-(1,1,2,2-tetrafluoroethoxy)phenyl)amino)carbonyl)-benzamide, 2,6-dibromo-N-(((4-(1,1,2,2-tetrafluoroethoxy)phenyl)amino)carbonyl)-benzamide, 2,6-dichloro-N-(((4-(2,2-dichloro-1,1-difluoroethoxy)phenyl)methylamino)carbonyl)-benzamide, 2,6-difluoro-N-(((4-(2,2-dichloro-1,1-difluoroethoxy)phenyl)methylamino)carbonyl)-benzamide, 2-bromo-N-(((4-(1,1,2,2-tetrafluoroethoxy)phenyl)amino)carbonyl)-benzamide, 2,6-dichloro-N-(((3-(2,2-dichloro-1,1-difluoroethoxy)phenyl)amino)carbonyl)-benzamide, 2-chloro-N-(((4-(2,2-dichloro-1,1-difluoroethoxy)phenyl)methylamino)carbonyl)-benzamide, 2,6-difluoro-N-(((3-(2,2-dichloro-1,1- difluoroethoxy)phenyl)amino)carbonyl)-benzamide, 2,6-difluoro-N-(((2-(2,2-dichloro-1,1-difluoroethoxy)-phenyl)amino)carbonyl)-benzamide, 2-trifluoromethyl-N-(((4-(2,2-dichloro-1,1-difluoroethoxy)phenyl)methylamino)carbonyl)-benzamide, 2-fluoro-N-(((4-(1,1,2,2-tetrafluoroethoxy)phenyl)amino)carbonyl)-benzamide, 2,6-difluoro-N-(((4-((2,2-dichloro-1,1-difluoroethyl)thio)phenyl)amino)carbonyl)-benzamide, 2,6-difluoro-N-(((4-((1,1,2,2-tetrafluoroethyl)thio)phenyl)amino)carbonyl)-benzamide, 2,6-dichloro-N-(((4-((1,1,2,2-tetrafluoroethyl)thio)phenyl)amino)carbonyl)-benzamide, 2,6-dichloro-N-(((4-(2,2-dichloro-1,1-difluoroethoxy)phenyl)amino)carbonyl)-benzamide, 2,6-dichloro-N-(((4-(1,1,2,2-tetrafluoroethoxy)phenyl)amino)carbonyl)-benzamide and 2-chloro-N-(((4-(2,2-dichloro-1,1-difluoroethoxy)phenyl)amino)carbonyl)-benzamide.

2. The compound of claim 1 which is 2-Chloro-N-(((4-(trifluoromethoxy)phenyl)amino)carbonyl)-benzamide.

3. The compound of claim 1 which is 2-Trifluoromethyl-N-(((4-(trifluoromethoxy)phenyl)amino)carbonyl)-benzamide.

4. The compound of claim 1 which is 2,6-Dichloro-N-(((4-(2,2-dichloro-1,1-difluoroethoxy)phenyl)amino)carbonyl)-benzamide.

5. The compound of claim 1 which is 2,6-Dichloro-N-(((4-(1,1,2,2-tetrafluoroethoxy)phenyl)amino)carbonyl)-benzamide.

6. The compound of claim 1 which is 2,6-Difluoro-N-(((4-(1,1,2,2-tetrafluoroethoxy)phenyl)amino)carbonyl)-benzamide.

7. The compound of claim 1 which is 2,6-Difluoro-N-(((4-(2,2-dichloro-1,1-difluoroethoxy)phenyl)amino)carbonyl)-benzamide.

8. The compound of claim 1 which is 2,6-Difluoro-N-(((4-(trifluoromethoxy)phenyl)amino)carbonyl-benzamide.

9. The compound of claim 1 which is 2,6-Dichloro-N-(((4-(trifluoromethoxy)phenyl)amino)carbonyl)-benzamide.

10. The compound of claim 1 which is 2,6-Dimethoxy-N-(((4-(1,1,2,2-tetrafluoroethoxy)phenyl)amino)-carbonyl)-benzamide.

11. The compound of claim 1 which is 2,6-Dichloro-N-(((2-(2,2-dichloro-1,1-difluoroethoxy)phenyl)amino)-carbonyl)-benzamide.

12. The compound of claim 1 which is 2-Chloro-N-(((4-(2,2-dichloro-1,1-difluoroethoxy)phenyl)amino)-carbonyl)-benzamide.

13. The compound of claim 1 which is 2,6-Dichloro-N-(((4-(2,2-dichloro-1,1-difluoroethoxy)phenyl)amino)-carbonyl)-N-methylbenzamide.

14. The compound of claim 1 which is 2-Chloro-N-(4-(((2,2-dichloro-1,1-difluoroethylthio)phenyl)amino)carbonyl)-benzamide.

15. The compound of claim 1 which is 2,6-Dichloro-N-(((4-((2,2-dichloro-1,1-difluoroethyl)thio)phenyl)amino)carbonyl)-benzamide.

16. The compound of claim 1 which is 2-Chloro-N-(((2-(2,2-dichloro-1,1-difluoroethoxy)phenyl)amino)-carbonyl)-benzamide.

17. The compound of claim 1 which is 2-Chloro-N-(((4-(1,1,2,2-tetrafluoroethoxy)phenyl)amino)carbonyl)-benzamide.

18. The compound of claim 1 which is 2,6-Dibromo-N-(((4-(1,1,2,2-tetrafluoroethoxy)phenyl)amino)carbonyl)-benzamide.

19. The compound of claim 1 which is 2,6-Dichloro-N-(((4-(2,2-dichloro-1,1-difluoroethoxy)phenyl)methylamino)carbonyl)-benzamide.

20. The compound of claim 1 which is 2,6-Difluoro-N-(((4-(2,2-dichloro-1,1-difluoroethoxy)phenyl)methylamino)carbonyl)-benzamide.

21. The compound of claim 1 which is 2-Bromo-N-(((4-(1,1,2,2-tetrafluoroethoxy)phenyl)amino)carbonyl)-benzamide.

22. The compound of claim 1 which is 2,6-Dichloro-N-(((3-(2,2-dichloro-1,1-difluoroethoxy)phenyl)amino)-carbonyl)-benzamide.

23. The compound of claim 1 which is 2-Chloro-N-(((4-(2,2-dichloro-1,1-difluoroethoxy)phenyl)methylamino)carbonyl)-benzamide.

24. The compound of claim 1 which is 2,6-Difluoro-N-(((3-(2,2-dichloro-1,1-difluoroethoxy)phenyl)amino)-carbonyl)-benzamide.

25. The compound of claim 1 which is 2,6-Difluoro-N-(((2-(2,2-dichloro-1,1-difluoroethoxy)phenyl)amino)-carbonyl)-benzamide.

26. The compound of claim 1 which is 2-Trifluoromethyl-N-(((4-(2,2-dichloro-1,1-difluoroethoxy)-phenyl)methylamino)carbonyl)-benzamide.

27. The compound of claim 1 which is 2-Fluoro-N-(((4-(1,1,2,2-tetrafluoroethoxy)phenyl)amino)carbonyl)-benzamide.

28. The compound of claim 1 which is 2,6-Difluoro-N-(((4-((2,2-dichloro-1,1-difluoroethyl)thio)phenyl)amino)carbonyl)-benzamide.

29. The compound of claim 1 which is 2,6-Difluoro-N-(((4-((1,1,2,2-tetrafluoroethyl)thio)phenyl)amino)carbonyl)-benzamide.

30. The compound of claim 1 which is 2,6-Dichloro-N-(((4-((1,1,2,2-tetrafluoroethyl)thio)phenyl)amino)carbonyl)-benzamide.

31. A composition for the control of insects comprising a suitable adjuvant and an insecticidally-effective amount of a compound of claim 1.

* * * * *